United States Patent
Chen et al.

(10) Patent No.: US 11,266,167 B2
(45) Date of Patent: Mar. 8, 2022

(54) **PREPARATION OF *MORTIERELLA ALPINA* CCFM698 THALLI AND APPLICATION THEREOF IN FEED ADDITIVE**

(71) Applicant: Jiangnan University, Wuxi (CN)

(72) Inventors: Haiqin Chen, Wuxi (CN); Yongquan Chen, Wuxi (CN); Wei Chen, Wuxi (CN); Chengfeng Ge, Wuxi (CN); Xin Tang, Wuxi (CN); Zhennan Gu, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 424 days.

(21) Appl. No.: 16/390,947

(22) Filed: Apr. 22, 2019

(65) Prior Publication Data

US 2019/0246663 A1 Aug. 15, 2019

Related U.S. Application Data

(63) Continuation of application No. PCT/CN2018/072401, filed on Jan. 12, 2018.

(30) Foreign Application Priority Data

Jan. 13, 2017 (CN) .......................... 201710024478.1

(51) Int. Cl.
*A23K 10/14* (2016.01)
*C12N 1/14* (2006.01)
*A23K 20/158* (2016.01)
*A23K 50/75* (2016.01)

(52) U.S. Cl.
CPC ............ *A23K 10/14* (2016.05); *A23K 20/158* (2016.05); *A23K 50/75* (2016.05); *C12N 1/14* (2013.01); *C12N 2500/05* (2013.01); *C12N 2500/34* (2013.01); *C12N 2500/76* (2013.01)

(58) Field of Classification Search
CPC ...... A23K 10/14; A23K 20/158; A23K 20/24; A23K 50/75; A23L 33/12; C12N 1/14; C12N 2500/05; C12N 2500/34; C12N 2500/76; C12N 9/0071; C12Y 114/19
See application file for complete search history.

(56) References Cited

U.S. PATENT DOCUMENTS

| 2007/0082008 A1* | 4/2007 | Harel | ................... A23K 20/142 |
| | | | 424/195.16 |
| 2008/0020033 A1* | 1/2008 | Kawashima | .............. A23J 7/00 |
| | | | 424/455 |

FOREIGN PATENT DOCUMENTS

| CN | 104630077 A | 5/2015 |
| CN | 105647822 A | 6/2016 |
| CN | 106636236 A | 5/2017 |
| CN | 106754436 A | 5/2017 |
| WO | 2015005466 A1 | 1/2015 |

* cited by examiner

*Primary Examiner* — Blaine Lankford
(74) *Attorney, Agent, or Firm* — IPRO, PLLC; Na Xu

(57) ABSTRACT

The present disclosure discloses preparation of *M. alpina* CCFM698 thalli and application thereof in a feed additive, and belongs to the field of biological engineering and feed additives. The total fatty acid content of the *M. alpina* dried thalli obtained by the present disclosure is 30%-40% by weight of the dried thalli, and the EPA content is 24% or more by weight of total fatty acids. The dosage of the dried thalli in the feed in the disclosure is 0.5-1.5% of the total weight of the basal feed. The thallus feed additive is reasonable in fatty acid composition and very high in EPA content and can be used for producing high-DHA eggs which are beneficial to body health of eaters. The DHA content in each of eggs laid by laying hens fed with the feed containing the feed additive of the present disclosure reaches about 120 mg which is obviously higher than that in the prior art.

7 Claims, 2 Drawing Sheets

PREPARATION OF *MORTIERELLA ALPINA* CCFM698 THALLI AND APPLICATION THEREOF IN FEED ADDITIVE

TECHNICAL FIELD

The present disclosure relates to preparation of *Mortierella alpina* (*M. alpina*) CCFM698 thalli and application thereof in a feed additive, particularly relates to *M. alpina* thalli with high total fatty acid content and high EPA content, a production method thereof and application thereof as the feed additive, and belongs to the fields of biological engineering and feed additives.

BACKGROUND

Polyunsaturated fatty acids (PUFAs) can be divided into an ω-3 series, an ω-6 series, an ω-9 series, and the like. The ω-3 series PUFAs mainly include alpha-linolenic acid (ALA), eicosapentaenoic acid (EPA), docosapentaenoic acid (DPA) and docosahexaenoic acid (DHA). The EPA has special physiological functions of resisting blood coagulation, resisting cancers, resisting inflammation, preventing cardiovascular diseases, reducing blood fat and the like, and can be widely applied to industries of medicine and health products, foods and feeds. The biological sources of the EPA mainly include marine fishes and products obtained by microbial fermentation. The microbial fermentation method for producing the EPA is rich in raw material, short in period, cheap in price, small in floor space, free of weather effect and the like, and gets more and more attentions. At present, commercial products for producing the EPA by the microbial fermentation method are New Harvest™ EPA oil and Verlasso® salmon reported by the DuPont Company, and the used strain is a *Yarrowia lipolytica* genetic engineering strain.

The *M. alpina* is rich in grease content, and the wild *M. alpina* can synthesize the EPA with lower yield at a low temperature. The *M. alpina* MA-oPpFADS17 is characterized in that the ω-3 fatty acid desaturase derived from *Phytophthora parasitica* (*P. parasitica*) is over-expressed in the wild *M. alpina*, and finally, an *M. alpina* recombinant strain successfully expressing candidate ω-3 fatty acid desaturase is obtained. The recombinant strain is inoculated in a Broth culture medium to be subjected to shake culture for 7 d at 28° C. and 200 rpm, and the measuring result shows that the yield of the EPA (C20:5) reaches 617.1 mg/L accounting for 18.7% of total fat (TFA). In order to further increase the yield of the EPA, the conditions for producing the EPA by fermentation of the *M. alpina* need to be improved.

SUMMARY

In order to overcome the defects of the prior art, the present disclosure provides a feed additive capable of increasing the DHA content in eggs.

The feed additive is characterized in that the fermentation culture technology of an *M. alpina* strain is optimized to obtain *M. alpina* thalli accumulating EPA in a large amount under normal temperature conditions so as to be applied to the feed additive.

The *M. alpina* strain is a recombinant *M. alpina* MA-oPpFADS17-4 (the recombinant *M. alpina* MA-oPpFADS17-4 is also known as *M. alpina* CCFM698), and is the recombinant *M. alpina* over-expressing the ω-3 desaturase oPpFADS17 gene derived from *P. parasitica*. The construction method of the *M. alpina* strain refers to the Chinese disclosure patent application of which the publication number is CN105647822A and the title of disclosure is a recombinant *M. alpina* strain over-expressing ω-3 desaturase derived from *P. parasitica*, a construction method thereof and application thereof. The *M. alpina* strain is preserved on Jan. 18, 2016 in the CGMCC, Institute of Microbiology, Chinese Academy of Sciences, No. 3, No. 1 Courtyard, Beichen West Road, Chaoyang District, Beijing, and the preservation number is CGMCC No. 11820.

In an example of the present disclosure, the *M. alpina* thalli serve as the feed additive in a form of dried thalli.

In an example of the present disclosure, the total fatty acid content of the dried thalli is 30%-40% by weight of the dried thalli, and the EPA content is 24% or more by weight of total fatty acids.

In an example of the present disclosure, the dosage of the dried thalli in the feed is 0.5-1.5% of the total weight of the basal feed.

In an example of the present disclosure, the fermentation technology of the *M. alpina* strain comprises the following steps:

(1) inoculating a two-generation-activated *M. alpina* CCFM698 strain into a fermentation culture medium according to the inoculation amount of 1% by weight, and then, performing fermentation for 7 d under the conditions that the temperature is 28° C. and the rotation speed is 200 rpm;

the fermentation culture medium is prepared from the following ingredients:

| | |
|---|---:|
| glucose or corn starch | 50 g/L |
| bean meal extract or bean meal | 10-70 g/L |
| potassium nitrate | 0-10 g/L |
| phosphate | 1 g/L |
| magnesium sulfate heptahydrate | 0.25 g/L | the balance of water;

the pH value of the fermentation culture medium is 6.0-8.0;

the phosphate is selected from one of potassium dihydrogen phosphate, dipotassium hydrogen phosphate, sodium dihydrogen phosphate and disodium hydrogen phosphate;

(2) filtering the thalli obtained by fermentation in the step (1) by using a 200-mesh standard sieve, and then, washing the filtered thalli with clear water to obtain wet thalli;

(3) drying the wet thalli obtained in the step (2) to obtain the dried thalli.

In an example of the present disclosure, the preparation method of the bean meal extract comprises the following steps: taking 1 part by weight of bean meal, adding 5 parts by weight of water, boiling the water for 10-30 min, filtering the obtained product with double-layer gauze, discarding the filter residue, and cooling the obtained filtrate to room temperature, thereby obtaining the bean meal extract.

In an example of the present disclosure, the bean meal is a by-product obtained after extraction of soybean oil from soybeans, and the bean meal has an irregular fragment shape, has a color from light yellow to light brown and has fragrance of roasted soybeans. The bean meal is a product which can be purchased on the market, such as bean meal products sold by Sinograin (Zhenjiang) Oils & Grains Co., Ltd.

In an example of the present disclosure, the drying process in the step (3) can be implemented by keeping the wet thalli at 50-60° C. for 5-10 h.

In an example of the present disclosure, in the step (3), the drying process can be replaced by a freeze-drying process to obtain the freeze-dried thalli of the *M. alpina*. The freeze-drying process is implemented by a freeze dryer and comprises the following procedures: keeping the wet thalli at −40° C. for 4 h, freezing the thalli at −30° C. for 15 h, freezing the thalli at −10° C. for 15 h, then keeping the thalli at 10° C. for 4 h, and finally, keeping the thalli at 20° C. for 4 h to obtain the freeze-dried thalli.

The *M. alpina* CCFM698 thallus feed additive is reasonable in fatty acid composition and very high in EPA content and can be used for producing high-DHA eggs which are beneficial to body health of eaters. The additive has the advantages of high use safety, high content of PUFAs, reasonable fatty acid composition, and the like. Under the condition that egg laying performance parameters are not lowered, the ratio of ω-3 to ω-6 is maintained in a reasonable scope, thereby generating beneficial effects for body health.

In addition, the thallus feed additive of the present disclosure has high safety, the wild strain of the thalli passes formal safety assessment, and the production safety of the thalli is ensured. In the obtained feed additive, the EPA content accounts for 24% of the total fat at normal temperature, and the total fatty acid content accounts for 40% of the total weight of the thalli, so that the *M. alpina* strain of the present disclosure has maximum EPA yield at normal temperature in literature reports at present. The DHA content in each of eggs laid by laying hens fed with the feed containing the feed additive of the present disclosure reaches about 120 mg which is obviously higher than that in the prior art.

On the other hand, the present disclosure improves the fermentation technology, and the culture medium used for producing the thallus feed additive contains cheap glucose and bean meal which have lower market prices and are easy to obtain, so that the production cost is low. Furthermore, the fermentation of the thallus feed additive is performed at normal temperature instead of low temperature, so that the fermentation cost is greatly lowered.

DETAILED DESCRIPTION

Figure 1:
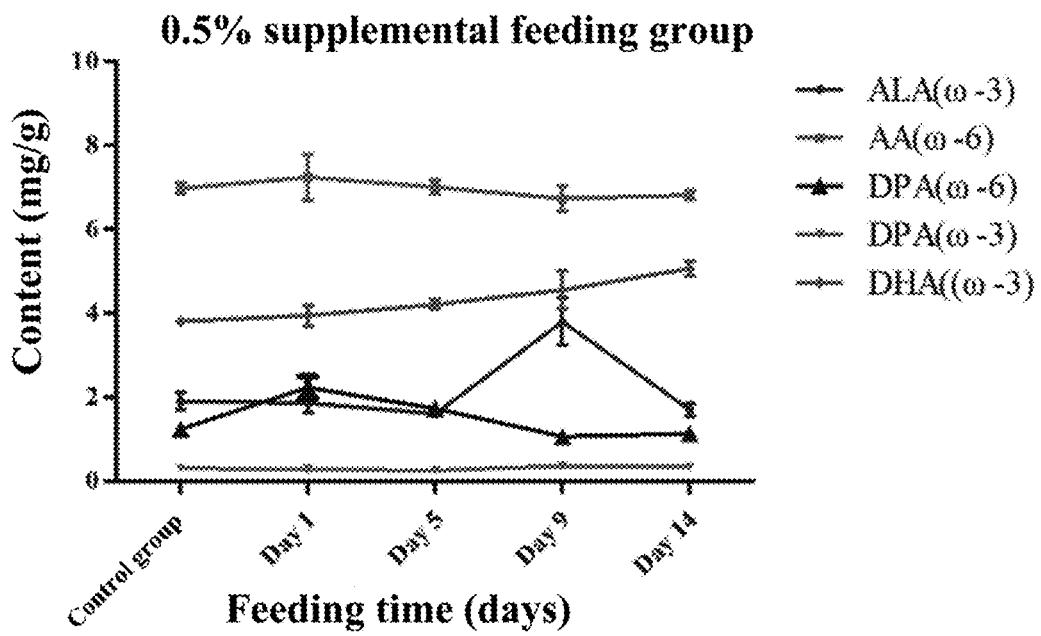
FIG. 1 shows the change of each main fatty acid in the supplemental feeding period of 0.5% *M. alpina* thalli in the example 7.

In the present disclosure, unless otherwise specified, "%" for indicating the concentration is a percentage by weight, or "parts" are parts by weight.

The culture equipment used in the present disclosure is a vibration incubator (model: ZQZY-70B) sold by Shanghai Zhichu Instrument Co., Ltd.

In the present disclosure, the freeze-drying process is implemented by using a freeze dryer (model: FreeZone 6) sold by LABCONCO.

Example 1: Determination of Glucose Concentration in Fermentation Culture Medium The *M. alpina* CCFM698 is inoculated into an activated culture medium according to the inoculation amount of 1% and is activated for 36 h and two generations under the conditions that the temperature is 28° C. and the rotation speed is 200 rpm.

A basal fermentation culture medium is prepared from: 20 g/L glucose, 5 g/L yeast extract, 10 g/L potassium nitrate, 1 g/L potassium dihydrogen phosphate, and 0.25 g/L magnesium sulfate heptahydrate. A 1M HCl aqueous solution and a 1M NaOH aqueous solution are adopted to adjust the pH value to 6.0, and sterilization is performed for 20 min at 115° C. to obtain the activated culture medium.

The glucose in the basal fermentation culture medium is set to 40 g/L, 50 g/L and 60 g/L, the wild *M. alpina* (MA) is used as a contrast, other conditions are not changed, and the experimental strain, namely *M. alpina* CCFM698, is subjected to normal temperature fermentation for 7 d at 28° C. so as to measure the fatty acid content in thalli according to different glucose concentrations in the fermentation culture medium.

The fatty acid measuring method refers to literatures:
Wang L, Chen W, Feng Y, et al. Genome characterization of the oleaginous fungus *Mortierella alpina*. Plos One, 2011, 6(12): e28319.

After total fatty acids are measured, the corresponding fatty acid contents are added to obtain the content of PUFAs.

TABLE 1

Influences of different initial glucose concentrations on production of EPA by fermentation of *M. alpina* CCFM698

| Different addition concentrations of glucose (g/L) | Dry weight of thalli (g/L) | TFA (g/L) | EPA (mg/L) | AA (mg/L) |
| --- | --- | --- | --- | --- |
| 40 | $10.20 \pm 0.26^{bc}$ | $3.87 \pm 0.17^{b}$ | $1044.90 \pm 61.42^{b}$ | $368.36 \pm 24.68^{b}$ |
| 50 | $9.93 \pm 0.35^{b}$ | $4.04 \pm 0.18^{bc}$ | $1143.57 \pm 32.05^{b}$ | $375.49 \pm 13.41^{b}$ |
| 60 | $9.70 \pm 0.14^{a}$ | $3.17 \pm 0.19^{a}$ | $888.95 \pm 75.59^{a}$ | $252.20 \pm 45.38^{a}$ |

Note:
The data in the table is expressed as average value ± standard deviation, and the Tukey HSD method in SPSS is adopted for significance analysis.

Visibly, the strain can accumulate a large amount of EPA at normal temperature and has great advantages compared with the wild strain. In addition, by comparison, the glucose concentration of 50 g/L is most suitable for production of the EPA by the strain.

Example 2: Determination of Carbon Source Type in Culture Medium 50 g/L glucose in the basal fermentation culture medium is replaced respectively by corn starch, soluble starch, potato starch and a mixture of glucose and soluble starch in a weight ratio of 1:1, other ingredients and culture conditions in the culture medium are not changed, and the *M. alpina* CCFM698 is subjected to normal temperature fermentation for 7 d at 28° C. so as to measure the fatty acid content in a sample.

TABLE 2

Influences of different carbon source types on production
of EPA by fermentation of *M. alpina* CCFM698

| Different carbon source substrates | Dry weight of thalli (g/L) | TFA (g/L) | EPA (mg/L) | AA (mg/L) |
|---|---|---|---|---|
| Glucose | 10.13 ± 0.40$^b$ | 3.99 ± 0.05$^b$ | 1005.56 ± 13.55$^b$ | 392.76 ± 8.82$^b$ |
| Corn starch | 12.47 ± 0.32$^c$ | 4.86 ± 0.07$^c$ | 1151.52 ± 55.09$^{bc}$ | 648.62 ± 8.80$^c$ |
| Soluble starch | 10.20 ± 0.30$^b$ | 1.87 ± 0.03$^a$ | 579.08 ± 51.67$^a$ | 98.80 ± 9.01$^a$ |
| Potato starch | 6.73 ± 0.21$^a$ | 1.75 ± 0.02$^a$ | 582.38 ± 20.93$^a$ | 130.15 ± 19.06$^a$ |
| Glucose + soluble starch | 9.80 ± 0.26$^b$ | 3.84 ± 0.19$^b$ | 658.36 ± 40.48$^{ab}$ | 419.48 ± 15.65$^b$ |

It can be seen from the table that the *M. alpina* CCFM698 can utilize various starches as substrates for fermentation to produce fat according to different degrees, wherein the effects of the corn starch and the glucose are optimal, and the yield of the EPA is up to 1 g/L or more which is obviously higher than that obtained by other carbon sources.

Although the corn starch, the soluble starch and the potato starch are all starches, the potato starch and the soluble starch show an obvious result of reducing the yield of total fatty acid (TFA) and the EPA compared to the glucose, and the corn starch and the glucose can increase the yield of the TFA and the EPA to some extent.

Example 3: Determination of Organic Nitrogen Source

In the culture medium, on the premise that the carbon source is 50 g/L glucose, influences of yeast extract (organic nitrogen source, expensive) and bean meal extract (cheap) on production of fat by *M. alpina* are compared, wherein the concentration of the yeast extract is 5 g/L, the concentration of the bean meal extract is 50 g/L, other conditions are not changed, and the experimental strain, namely the *M. alpina* CCFM698, is subjected to normal temperature fermentation for 7 d at 28° C. so as to measure the fatty acid content in a sample.

TABLE 3

Influences of different organic nitrogen sources on production
of EPA by fermentation of *M. alpina* CCFM698

| Different organic nitrogen sources | Dry weight of thalli (g/L) | TFA (g/L) | EPA (mg/L) | AA (mg/L) |
|---|---|---|---|---|
| Yeast extract | 9.93 ± 0.35$^a$ | 4.04 ± 0.18$^a$ | 1143.57 ± 32.05$^a$ | 375.49 ± 13.41$^a$ |
| Bean meal extract | 12.40 ± 0.60$^b$ | 5.28 ± 0.15$^b$ | 1545.64 ± 46.98$^b$ | 350.52 ± 22.75$^a$ |

The results show that compared with the expensive yeast extract, when the bean meal extract is used as an organic nitrogen source, the bean meal extract is low in price, has a great effect on promoting growth of thalli, and greatly increases the yield of the EPA to 1545 mg/L.

Then, different addition concentrations of bean meal juice are further set to 10 g/L, 30 g/L, 50 g/L and 70 g/L respectively, other conditions are not changed, and the experimental strain, namely the *M. alpina* CCFM698, is subjected to normal temperature fermentation for 7 d at 28° C. so as to measure the fatty acid content in a sample.

TABLE 4

Influences of different bean meal juice concentrations on
production of EPA by fermentation of *M. alpina* CCFM698

| Bean meal juice concentration (g/L) | Dry weight of thalli (g/L) | TFA (g/L) | EPA (mg/L) | AA (mg/L) |
|---|---|---|---|---|
| 10 | 13.05 ± 0.21$^a$ | 4.07 ± 0.30$^a$ | 933.89 ± 44.26$^a$ | 159.11 ± 21.61$^a$ |
| 30 | 15.00 ± 0.14$^c$ | 6.37 ± 0.14$^c$ | 1857.26 ± 74.26$^b$ | 462.59 ± 19.60$^b$ |
| 50 | 15.10 ± 0.42$^c$ | 5.99 ± 0.56$^c$ | 1916.80 ± 24.05$^b$ | 464.11 ± 29.28$^b$ |
| 70 | 14.20 ± 0.31$^b$ | 5.21 ± 0.22$^b$ | 976.42 ± 32.91$^a$ | 164.45 ± 16.15$^a$ |

It can be seen that the bean meal extract of 10-70 g/L shows obvious favorable influences on production of the EPA by fermentation of the M. alpina strain, wherein the concentration is preferably 30-50 g/L. The bean meal extract of which the concentration is 50 g/L is suitable for production of fat by fermentation of the strain, and the yield of the EPA is maximum and reaches 1.9 g/L.

Example 4: Production of Thallus Feed Additive of Present Disclosure (1) High-Density Culture in Fermentor In order to obtain a sufficient amount of thallus feed additive, a fermentor is further used for culture, and the culture equipment is a 65 L airlift fermentor (model: SSTC-2005-11) sold by Bioengineering AG in Switzerland. Different from shake culture, in fermentor culture, in order to adapt to the fermentor technology, the inoculation amount is increased, the two-generation-activated M. alpina MA-oPp-FADS17 strain is inoculated into a high-density fermentation culture medium according to the inoculation amount (seed stock solution) of 10%, the pH value is maintained to be 6.0, the ventilation capacity is 0.75 vvm, and the strain is fermented for 7 d at the room temperature of 28° C.

The used high-density fermentation culture medium is prepared from: 50 g/L glucose, 15 g/L bean meal, 5 g/L potassium nitrate, 2 g/L potassium dihydrogen phosphate, and 0.25 g/L magnesium sulfate heptahydrate.

In order to meet the needs of industrial production and lower the raw material cost and the thallus preparation cost, in this example, the bean meal instead of the bean meal extract is selected as an organic nitrogen source, and a conventional thallus drying method is adopted for subsequent drying operation of wet thalli.

(2) Collection of Thalli and Preparation of Feed Additive

The thalli fermented in the step (1) are filtered with a 200-mesh standard sieve, the filtered thalli are washed with clear water until the filtrate is clear and transparent to obtain wet thalli, the wet thalli are dried at 60° C., simultaneously a freeze-drying process is used for preparing samples so as to adapt to laboratory conditions, and the effects of dried products and freeze-dried products are respectively measured.

The measuring results show that the obtained freeze-dried thalli (samples) and dried thalli (feed additive) have consistent indexes, the moisture content is less than 1% (almost absolutely dried material), the absolute content of the total fatty acids reaches 6.17 g/L, and the absolute content of the EPA reaches 1.4 g/L.

The fatty acid composition and content of the thallus feed additive are measured as follows:

TABLE 5

Fatty acid composition and content of thallus feed additive

| Fatty acid | Percentage of fatty acid accounting for total fat (%) | Fatty acid content (mg/g) |
| --- | --- | --- |
| C14:0 | 0.67 ± 0.02 | 2.62 ± 0.08 |
| C16:0 | 9.42 ± 0.32 | 37.03 ± 1.26 |
| C17:0 | 0.24 ± 0.01 | 0.93 ± 0.04 |
| C18:0 | 15.81 ± 1.04 | 62.17 ± 4.09 |
| C18:1 | 16.77 ± 0.89 | 65.96 ± 3.50 |
| C18:2 (ω-6, LA) | 8.56 ± 0.42 | 33.64 ± 1.65 |
| C18:3 (ω-6, GLA) | 3.02 ± 0.13 | 11.89 ± 0.51 |
| C20:0 | 1.36 ± 0.05 | 5.34 ± 0.20 |
| C20:1 | 0.80 ± 0.01 | 3.13 ± 0.04 |
| C20:2 | 0.77 ± 0.02 | 3.04 ± 0.08 |
| C20:3 (ω-6, DGLA) | 0.35 ± 0.00 | 1.37 ± 0.02 |
| C22:3 | 2.76 ± 0.05 | 10.84 ± 0.20 |
| C20:4 (ω-6, AA) | 12.48 ± 0.74 | 49.08 ± 2.91 |
| C20:5 (ω-3, EPA) | 23.70 ± 1.13 | 93.20 ± 4.44 |
| C22:0 | 2.42 ± 0.02 | 9.51 ± 0.08 |
| C24:0 | 1.88 ± 0.04 | 7.40 ± 0.16 |
| Total ω-6 PUFAs | 24.41 ± 0.98 | 95.98 ± 3.85 |
| Total ω-3 PUFAs | 23.70 ± 1.02 | 93.27 ± 4.01 |

Visibly, the types of the fatty acids in the feed additive obtained by the present disclosure are richer, the content of PUFAs (including C18:2/C18:3/C20:2/C20:3/C22:3/C20:4/C20:5) accounts for 51.64% of the total fatty acid content, the content of the EPA having important physiological functions accounts for about 24% of the total fatty acid content and is obviously higher than 6.09% in CN104630077A, and the ratio of ω-3 to ω-6 is increased to about 1:1 and is also obviously better than that in the prior art.

Example 5: Laying Hen Feeding Experiment

According to the literatures, ω-3 PUFAs in an ordinary egg are mainly DHA accounting for 0.04% of the total weight of the whole egg, which is much different from the daily recommended intake (140-160 mg) of DHA.

Therefore, it is expected to increase the DHA content in the egg by improving the laying hen feed.

In order to more effectively explain the practicability of the thallus feed additive, firstly, the thallus feed additive is mixed with the basal feed by 0.5% or 1% or 1.5% respectively based on the total weight of the basal feed, and then, a series of animal experiments are adopted for verification. Specific examples, results and analysis of the animal experiments are as follows:

(1) Preparation of Thallus Feed

The basal feed is provided by Anhui Rongda Poultry Development Co., Ltd. (the fatty acid composition of the basal feed is as shown in table 8 below), and the thallus feed additive in the example 6 is added in a ratio of 0.5% or 1% or 1.5% of the total weight of the basal feed respectively so as to obtain the EPA thallus feed.

TABLE 6

Fatty acid composition of basal feed

| Fatty acid | Percentage of fatty acid accounting for total fat (%) | Fatty acid content (mg/g) |
| --- | --- | --- |
| C16:0 | 11.69 | 5.23 |
| C18:0 | 2.38 | 1.06 |
| C18:1 | 33.59 | 15.02 |
| C18:2 (LA, ω-6) | 47.38 | 21.18 |
| C18:3 (ALA, ω-3) | 4.53 | 2.02 |

(2) Experiment Grouping and Design 60 25-week-old laying hens are selected and divided into four groups randomly, 15 laying hens form a group, and the four groups are respectively recorded as group A, group B, group C, and group D, wherein the group A is a control group, the group B, group C, and group D are experimental groups, and two groups of commercially available eggs from different sources are purchased as contrasts.

An experimental period is divided into an adaptation period, a test period, and an elution period. In 7 d of the adaptation period, the laying hens in each group are fed with the basal feed. In the test period, the laying hens in the group A are fed with the basal feed, the laying hens in the group B, group C, and group D are fed with a low dose (0.5% by weight of the basal feed), a medium dose (1% by weight of the basal feed), and a high dose (1.5% by weight of the basal feed) of the thallus feed additive respectively, and the feeding period is two weeks. In 10 d of the elution period, the laying hens in each group are fed with the basal feed.

(3) Feeding and Management Method

A feeding experiment is performed in Anhui Rongda Poultry Development Co., Ltd., a stable breeding mode is adopted for the laying hens, 14 h of light is provided for the laying hens per day (light can be supplemented), and each laying hen is fed with 120 g of feed per day and fed with sufficient water. The laying hens are fed twice per day at 8:00 and 16:00, and eggs are collected at 16:00 per day and are labeled.

(4) Measurement of Fatty Acids in Eggs

References of analysis methods for fatty acids in eggs:

Wang L, Chen W, Feng Y, et al. Genome characterization of the oleaginous fungus *Mortierella alpina*. Plos One, 2011, 6(12): e28319.

(5) Results and Analysis

The composition of fatty acids in yolk in each group at the end of the supplemental period is as shown in the table below.

the eggs in the group A is very high, so two kinds of eggs are randomly purchased from the market as contrasts. Compared with the commercially available eggs, the DHA content of the eggs laid by the laying hens fed with the basal feed containing the thallus feed additive of the present disclosure is increased by about four times, and thus the effect is obvious.

Figure 2:
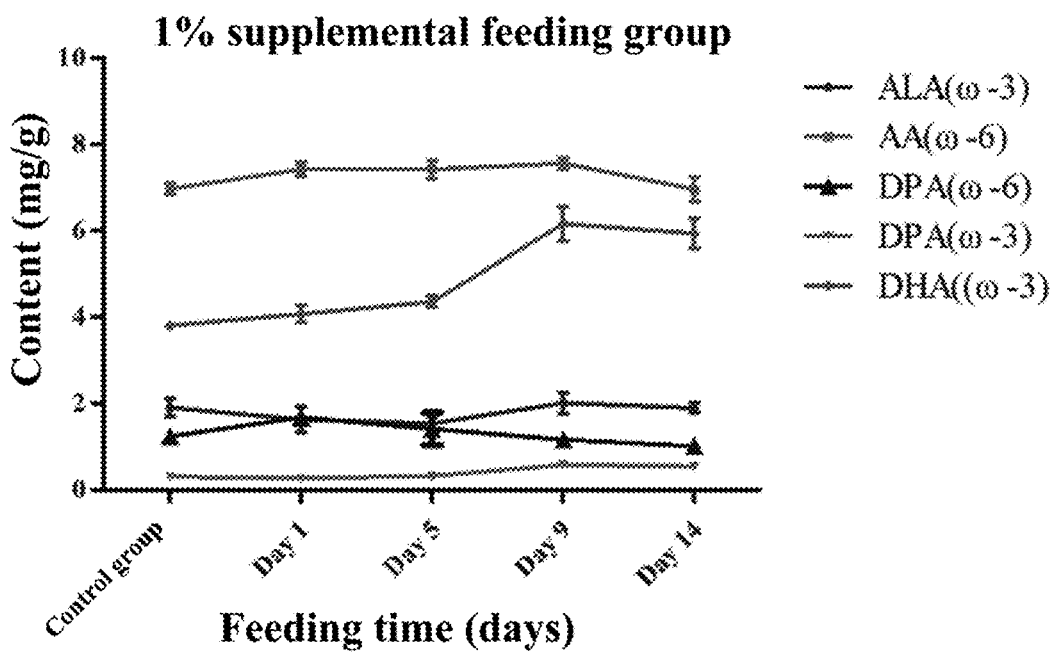
FIG. 2 shows the change of each main fatty acid in the supplemental feeding period of 1% *M. alpina* thalli in the example 7.
Figure 3:
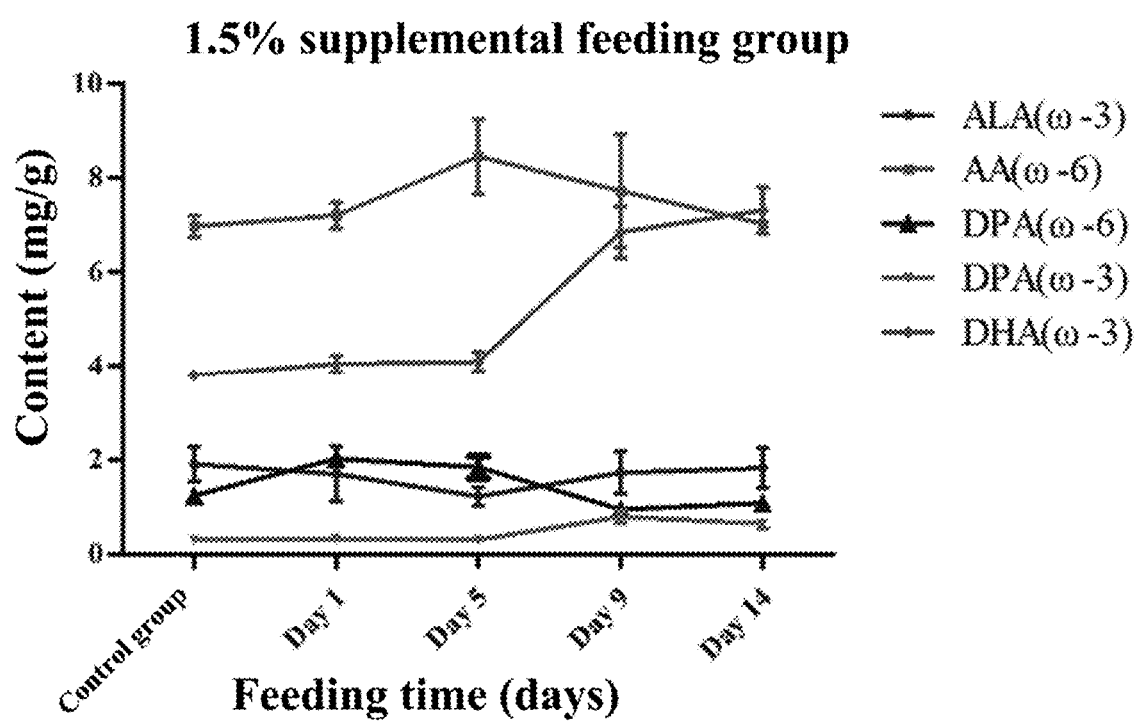
FIG. 3 shows the change of each main fatty acid in the supplemental feeding period of 1.5% *M. alpina* thalli in the example 7.

In addition, as shown in FIGS. 1-3, as the time for supplemental feeding increases, groups with different replenishment amounts have different peak times. It can be seen from FIG. 1, the DHA content of the yolk in the 0.5% supplemental feeding group shows a slow increase trend during the two-week supplemental period, and the increase of the DHA content is less. In FIG. 2, the yolk in the 1% supplemental feeding group reaches the peak around the tenth day and then has a slow decrease trend, and the DHA content is higher than that of the 0.5% supplemental feeding group. The change conditions of the DHA content of the yolk in the 1.5% supplemental feeding group can be obtained from FIG. 3: the accumulation of DHA in the first five days is less, the DHA content shows a rapid increase trend from the fifth to ninth days, and the DHA content shows a slow increase trend from the ninth to fourteenth days. After two weeks of supplement, the DHA content in the yolk reaches 7.31 mg/g, about 120 mg/egg, which is about four times higher than the DHA content of the commercially available eggs (the DHA content of the commercially available eggs is about 30 mg).

The calculation method of the DHA content in each egg is: DHA (mg/egg)=weight percentage of total fatty acid content of yolk×percentage of DHA accounting for total fat in yolk×1000×weight of yolk

TABLE 7

Measurement results of fatty acid content in yolk

| Fatty acid | A (mg/g) | B (mg/g) | C (mg/g) | D (mg/g) | Commercially available egg 1 (mg/g) | Commercially available egg 2 (mg/g) |
|---|---|---|---|---|---|---|
| C16:0 | 48.24 ± 3.05 | 42.19 ± 1.93 | 44.98 ± 2.16 | 45.62 ± 2.31 | 43.72 ± 1.71 | 47.48 ± 6.58 |
| C16:1 | 10.61 ± 1.21 | 10.86 ± 0.95 | 10.55 ± 0.56 | 10.44 ± 0.48 | 14.45 ± 1.21 | 12.17 ± 2.73 |
| C18:0 | 27.71 ± 1.89 | 25.11 ± 1.04 | 27.26 ± 0.84 | 28.18 ± 0.47 | 23.02 ± 0.81 | 24.09 ± 1.88 |
| C18:1 | 112.64 ± 7.90 | 98.13 ± 1.62 | 104.92 ± 3.47 | 111.08 ± 6.63 | 85.50 ± 4.50 | 84.14 ± 8.13 |
| C18:2 (ω-6, LA) | 32.21 ± 3.72 | 29.65 ± 3.50 | 32.08 ± 6.42 | 29.74 ± 2.27 | 31.08 ± 4.07 | 42.90 ± 0.65 |
| C18:3 (ω-6, GLA) | 0.32 ± 0.10 | 0.38 ± 0.05 | 0.35 ± 0.04 | 0.33 ± 0.02 | 0.37 ± 0.03 | 0.67 ± 0.07 |
| C18:3 (ω-3, ALA) | 1.87 ± 0.44 | 1.70 ± 0.24 | 1.90 ± 0.19 | 1.83 ± 0.42 | 1.38 ± 0.12 | 1.30 ± 0.06 |
| C20:3 (ω-6, DGLA) | 0.15 ± 0.03 | 0.16 ± 0.05 | 0.18 ± 0.03 | 0.19 ± 0.04 | 0.31 ± 0.03 | 0.20 ± 0.04 |
| C20:4 (ω-6, AA) | 7.23 ± 0.54 | 6.81 ± 0.18 | 6.96 ± 0.49 | 7.03 ± 0.09 | 6.19 ± 0.15 | 7.49 ± 1.43 |
| C22:5 (ω-6, DPA) | 1.14 ± 0.17 | 1.13 ± 0.18 | 1.01 ± 0.21 | 1.08 ± 0.11 | 1.93 ± 0.38 | 2.84 ± 0.44 |
| C22:5 (ω-3, DPA) | 0.28 ± 0.08 | 0.34 ± 0.06 | 0.54 ± 0.02 | 0.64 ± 0.10 | 0.23 ± 0.04 | 0.34 ± 0.04 |
| C22:6 (ω-3, DHA) | 3.92 ± 0.17 | 5.06 ± 0.31 | 5.94 ± 0.60 | 7.31 ± 0.49 | 1.88 ± 0.18 | 1.71 ± 0.32 |
| Total ω-6 PUFAs | 41.06 ± 3.61 | 38.12 ± 3.32 | 40.59 ± 7.01 | 38.37 ± 2.02 | 39.88 ± 4.63 | 54.09 ± 2.42 |
| Total ω-3 PUFAs | 6.07 ± 0.41 | 7.89 ± 0.23 | 8.39 ± 0.75 | 9.78 ± 0.58 | 3.48 ± 0.33 | 3.35 ± 0.25 |

It can be seen from the data in the table that based on the weight of the basal feed, the DHA accumulation amount of the yolk in the eggs obtained by adding 1.5% addition amount of the thallus feed additive is maximum, and compared with the contrast, the content is about twice that of the group A. A large amount of EPA in the thallus feed is converted into DHA of the yolk, thereby indicating that the yolk has the effect of enriching DHA.

According to the absolute content (unit: mg/g) of each fatty acid index in the eggs recorded in the table 7, the DHA content in an egg is about 120 mg which is much higher than the content (70 mg) recorded in CN104630077A. Considering that the ALA content in the basal feed for the group A is higher (see table 6) in the disclosure, the DHA content of In conclusion, the thallus feed additive of the present disclosure can be used for producing eggs with high DHA content and has high safety. The EPA content of the obtained feed additive can account for 24% of total fat at normal temperature, and the total fatty acid content reaches 40% of the total weight of the thalli.

The DHA content in each of eggs laid by laying hens fed with the feed containing the feed additive of the present disclosure reaches about 120 mg which is obviously higher than that in the prior art.

What is claimed is:

1. A method for preparing a chicken feed additive with high EPA content, wherein the method comprises the following steps:

(1) inoculating activated *M. alpina* over-expressing ω-3 fatty acid desaturase derived from *P. parasitica* into a fermentation culture medium, and then, performing fermentation for about 7 days under the condition that the temperature is 28-30° C.;

wherein the fermentation culture medium comprises:

| | |
|---|---|
| glucose or corn starch | 50 g/L, |
| bean meal extract or bean meal | 10-70 g/L, |
| potassium nitrate | 0-10 g/L, |
| phosphate | 1 g/L, |
| magnesium sulfate heptahydrate | 0.25 g/L; | wherein the pH value of the fermentation culture medium is 6.0;

and wherein the phosphate is selected from the group consisting of potassium dihydrogen phosphate, dipotassium hydrogen phosphate, sodium dihydrogen phosphate and disodium hydrogen phosphate;

(2) filtering the thalli obtained by the fermentation in the step (1) by using a 200-mesh standard sieve, and then, washing the filtered thalli with clear water to obtain wet thalli;

(3) drying the wet thalli obtained in the step (2) to obtain *M. alpina* dried thalli, namely the chicken feed additive.

2. The method for preparing the chicken feed additive with high EPA content according to claim 1, wherein the bean meal extract or the bean meal in the fermentation culture medium is 50 g/L.

3. The method for preparing the chicken feed additive with high EPA content according to claim 1, wherein the *M. alpina* over-expressing ω-3 fatty acid desaturase derived from *P. parasitica* is preserved on Jan. 18, 2016 in China General Microbiological Culture Collection Center (CGMCC), Institute of Microbiology, Chinese Academy of Sciences, No. 3, No. 1 Courtyard, Beichen West Road, Chaoyang District, Beijing, China, and the preservation number is CGMCC No. 11820.

4. The method for preparing the chicken feed additive with high EPA content according to claim 1, wherein the potassium nitrate in the fermentation culture medium is 10 g/L.

5. The method for preparing the chicken feed additive with high EPA content according to claim 1, wherein the preparation method of the bean meal extract comprises the following steps: taking 1 part by weight of bean meal, adding 5 parts by weight of water, and boiling the water for 10-30 min; filtering the obtained product with double-layer gauze, discarding the filter residue, and cooling the obtained filtrate to room temperature, thereby obtaining the bean meal extract.

6. The method for preparing the chicken feed additive with high EPA content according to claim 1, wherein in the step (3), the drying process is implemented by keeping the wet thalli at 50-60° C. for 5-10 h.

7. The method for preparing the chicken feed additive with high EPA content according to claim 6, further comprising a freeze-drying process in step (3) to obtain the *M. alpina* thalli; wherein the freeze-drying process is implemented by a freeze dryer and comprises the following procedures: keeping the wet thalli at −40° C. for 4 h, freezing the thalli at −30° C. for 15 h, freezing the thalli at −10° C. for 15 h, then keeping the thalli at 10° C. for 4 h, and finally, keeping the thalli at 20° C. for 4 h to obtain freeze-dried thalli.

* * * * *